United States Patent
Berkheimer

(10) Patent No.: US 10,143,685 B2
(45) Date of Patent: Dec. 4, 2018

(54) PARENTERAL AND TOPICAL COMPOSITIONS FOR PAIN

(71) Applicant: David Berkheimer, Duncansville, PA (US)

(72) Inventor: David Berkheimer, Duncansville, PA (US)

( * ) Notice: Subject to any disclaimer, the term of this patent is extended or adjusted under 35 U.S.C. 154(b) by 0 days.

(21) Appl. No.: 15/546,279

(22) PCT Filed: Jan. 28, 2016

(86) PCT No.: PCT/US2016/015241
§ 371 (c)(1),
(2) Date: Jul. 25, 2017

(87) PCT Pub. No.: WO2016/123270
PCT Pub. Date: Aug. 4, 2016

(65) Prior Publication Data
US 2018/0000804 A1 Jan. 4, 2018

Related U.S. Application Data

(60) Provisional application No. 62/108,763, filed on Jan. 28, 2015, provisional application No. 62/267,688, filed on Dec. 15, 2015.

(51) Int. Cl.
| | | |
|---|---|---|
| *A61K 31/445* | (2006.01) | |
| *A61K 9/19* | (2006.01) | |
| *A61K 31/4168* | (2006.01) | |
| *A61K 31/137* | (2006.01) | |
| *A61K 31/135* | (2006.01) | |
| *A61K 31/573* | (2006.01) | |
| *A61K 31/407* | (2006.01) | |
| *A61K 9/00* | (2006.01) | |

(52) U.S. Cl.
CPC .......... *A61K 31/445* (2013.01); *A61K 9/0019* (2013.01); *A61K 9/19* (2013.01); *A61K 31/135* (2013.01); *A61K 31/137* (2013.01); *A61K 31/407* (2013.01); *A61K 31/4168* (2013.01); *A61K 31/573* (2013.01)

(58) Field of Classification Search
None
See application file for complete search history.

(56) References Cited

U.S. PATENT DOCUMENTS

2011/0293749 A1 12/2011 Lo et al.
2013/0116215 A1 5/2013 Coma et al.

OTHER PUBLICATIONS

Masahiko et al., Knee Surgery, Sports Traumatology, Arthroscopy: Official Journal of the ESSKA (2014), 22(7), pp. 1638-1643.*
Denise McCarthy and Gabriella Iohom, Local Infiltration Analgesia for Postoperative Pain Control following Total Hip Arthroplasty: A Systematic Review, Anesthesiology Research and Practice, 2012, pp. 1-9, vol. 2012.
C. J. L. McCartney and G. A. McLeod, Local infiltration analgesia for total knee arthroplasty, British Journal of Anaesthesia 2011, pp. 487-489, vol. 107 (4).
P.A. Vieira, I. Pulai, G.C. Tsao, P, Manikantan, B. Keller, N.R. Connelly. Dexamethasone with bupivacaine increases duration of analgesia in ultrasound-guided interscalene brachial plexus blockade. Eur J Anaesthesiol, 2010, pp. 288,vol. 27.
K. C. Cummings III, D. E. Napierkowski, I. Parra-Sanchez, A. Kurz, J. E. Dalton, J. J. BREMS5 and D. I. Sessler. Effect of dexamethasone on the duration of interscalene nerve blocks with ropivacaine or bupivacaine. Br. J. Anaesth, 2011, pp. 446-453, vol. 107(3).
V. Umbrain, C. Sneyers, P. Matagne, M. Matic, M. La Meir. IV, paravertebral or epidural anesthesia to treat pain after hybrid atrial fibrillation (AF) ablation surgery? European Journal of Anaesthesiology, Jun. 2014, pp. 226-227, vol. 31 e-Supplement 52, Lippincott Williams & Wilkins.
Edward R. Mariano, Brett Miller, Francis V. Salinas, The Expanding Role of Multimodal Analgesia in Acute Perioperative Pain Management, Advances in Anesthesia, 2013, pp. 119-136, vol. 31.

* cited by examiner

*Primary Examiner* — Brian J Davis
(74) *Attorney, Agent, or Firm* — The Fedde Law Firm; Kenton Fedde; Nathaniel Fedde

(57) ABSTRACT

This invention provides compositions, kits containing compositions, and methods for their use in treating subjects with pain. Instant compositions comprise two or more long acting aminoamide local anesthetics, at least one NSAID, at least one corticosteroid, at least one alpha-2 ($\alpha$2) adrenergic receptor agonist, at least one N-methyl-D aspartate receptor antagonist, and optionally, epinephrine. Instant compositions are useful for infiltration anesthesia, field block anesthesia, regional anesthesia, peripheral nerve block, plexus anesthesia, epidural (or extradural) anesthesia, spinal anesthesia, local anesthesia, and transincision catheter anesthesia. The instant compositions have one or more superior properties of analgesia, duration of analgesia, safety, narcotic sparing, and motor sparing properties.

19 Claims, No Drawings

PARENTERAL AND TOPICAL COMPOSITIONS FOR PAIN

CROSS-REFERENCE TO RELATED APPLICATIONS

This application claims priority to U.S. Provisional Application Ser. No. 62/108,763 filed 28 Jan. 2015 and U.S. Provisional Application Ser. No. 62/267,688 filed 15 Dec. 2015, both of which are hereby incorporated by reference herein in their entirety.

TECHNICAL FIELD

The instant invention relates generally to an analgesic and anesthetic composition and use. More specifically, this invention relates to an analgesic and anesthetic composition to localize and numb the nerves of the user while maintaining motor function.

BACKGROUND

The management of pain (e.g. postoperative pain associated with surgery or joint replacement surgery) is often the most challenging and troublesome aspects of medical care. Inadequate pain control can be a source of significant anxiety and concern on the part of patients and their families and adversely affect recovery, rehabilitation, and need for homecare.

Current protocols for pain management incorporate various combinations of parenteral narcotics, regional anesthesia and nerve blocks. During the first 24-48 hours after surgery, narcotics are often required along with typical side effects such as nausea, itching, vomiting, drowsiness, urinary retention and ileus, respiratory depression, and even death. Regional anesthesia and nerve blocks may be associated with temporary or permanent neurologic dysfunction.

Analgesics and anesthetics are used to dull the pain receptors by controlling nerve output to the user's brain. The use of these traditional pain and sensory moderators allows doctors and medical staff to suppress a patient's reactions during surgeries and other invasive procedures to carry out the procedure correctly. The necessary dosage for these chemical compounds varies depending on physical characteristics of the patient, such as metabolism, weight, and body type. These chemical compounds, when used in a proper surgical setting, leave the patient without the ability to control the parts of the body that are numbed for some time after the surgery. This length of time which the patient cannot move various parts of their body requires the patients to remain in the hospital for the day or overnight. Some procedures may allow the patient to move much sooner than the anesthetics or would normally allow.

What is needed in the art are compositions and methods of providing better pain control and allow the patient mobility (e.g. after surgical procedures), reduced need for narcotics, and that allow the patient to return home the same day with full motor function.

SUMMARY OF THE INVENTION

This invention provides pharmaceutical compositions and methods of providing pain control, such compositions comprising:
a. two or more long acting aminoamide local anesthetics
b. at least one NSAID;
c. at least one corticosteroid;
d. at least one alpha-2 ($\alpha_2$) adrenergic receptor agonist,
e. at least one N-methyl-D aspartate receptor antagonist, and
f. optionally, epinephrine.

The compositions of the instant invention are useful for analgesia and, more specifically, for analgesia acting on the peripheral system or acting on a combination of the peripheral system and the central nervous system; e.g. periarticularly accompanying arthroplasty. Accordingly, the present invention also provides a method of providing analgesia comprising administering a present composition to a subject in need thereof.

DETAILED DESCRIPTION OF THE INVENTION

As used here, the following definitions and abbreviations apply.

"Components" means any of the components of the present invention (e.g. long acting aminoamide local anesthetics, NSAIDs, corticosteroids, $\alpha_2$ adrenergic receptor agonists, N-methyl-D aspartate receptor antagonists, epinephrines, and excipients). Components, according to the present invention, include any of the useful forms of the components such as polymorphs, crystal habits thereof, prodrugs and isomers thereof (including optical, geometric and tautomeric isomers), enantiomers, salts, solvates and complexes thereof and solvates and complexes of salts thereof.

"Exemplary" (or "e.g." or "by example") means a non-limiting example.

"Instant" refers to the present invention, e.g. instant NSAID means an NSAID as taught in this present specification according to the instant invention.

"Long acting aminoamide local anesthetics" means a local anesthetic that comprises a lipophilic moiety in amide linkage to a hydrophilic moiety, wherein the anesthetic acts by blocking Na+ channels when the channel is open. Typically, the active form of the anesthetic is the charged form and works without loss of consciousness and the duration of anesthesia or analgesia of four hours or more or optionally 6 hours or more or optionally 8 hours or more.

"Percent" (or %), when in reference to a component of the present inventions, means (when not otherwise defined or repugnant to the context) means % wt/% of the total volume of the instant composition.

Formulations

In one embodiment, the composition comprises:
a. two or more long acting aminoamide local anesthetics selected from the group consisting of ropivicaine, etidocaine, bupivicaine [e.g. R(+) or racemic RS (−)] or levobupivicaine [S(−) enantiomer], lidocaine, mepivacaine, prilocaine, dibucaine, and articaine.
b. at least one NSAID selected from the group consisting of ketorolac, ibuprofen, and indomethacin;
c. a corticosteroid selected from the group consisting of dexamethasone, methylprednisone, triamcinolone, and prednisolone;
d. at least one $\alpha_2$ adrenergic receptor agonist selected from the group consisting of clonidine, dexmedetomidine, xylazine, detomidine, guanfacine, guanabenz, medetomidine, and methyldopa;
e. at least one N-methyl-D aspartate receptor antagonist selected from the group consisting of ketamine, tramadol, and methadone; and
f. optionally, epinephrine.

In another embodiment, the composition comprises:
a. one or more long acting aminoamide local anesthetics selected from the group consisting of ropivicaine and etidocaine;
b. one or more long acting aminoamide local anesthetics selected from the group consisting of bupivicaine and levobupivicaine
c. at least one NSAID selected from the group consisting of ketorolac and ibuprofen;
d. at least one corticosteroid selected from the group consisting of dexamethasone and methylprednisone;
e. at least one $\alpha_2$ adrenergic receptor agonist selected from the group consisting of clonidine and dexmedetomidine;
f. at least one N-methyl-D aspartate receptor antagonist selected from the group consisting of ketamine and tramadol; and
g. optionally, epinephrine.

In another embodiment, the present compositions comprise ropivacaine, bupivacaine, ketorolac, clonidine, dexamethasone, ketamine, and optionally epinephrine. Combined with the teachings herein, the concentrations of these components can be determined by the skilled artisan. In one embodiment, each of the components can be formulated to the concentrations set forth in Table 1 ranging from the low-dose to the high dose.

TABLE 1

| Component | Low dose—Formula 001 % wt/total composition vol | High dose Formula 002 % wt/total composition vol |
|---|---|---|
| Ropivicaine | 0.1125 (1.125 mg/ml) | 0.25 (2.5 mg/ml) |
| Bupivicaine | 0.1125 (1.125 mg/ml) | 0.25 (2.5 mg/ml) |
| Ketorolac | 0.01 (100 µg/ml) | 0.04 (400 µg/ml) |
| Dexamethasone | 0.002 (20 µg/ml) | 0.01 (100 µg/ml) |
| Clonidine | 0.00005 (0.5 µg/ml) | 0.0002 (2 µg/ml) |
| Ketamine | 0.005 (50 µg/ml) | 0.05 (500 µg/ml) |
| Epinephrine | 0.0001 (1 µg/ml) | 0.0003 (3 µg/ml) |

In other embodiments (e.g. for parenteral administration), each of the components of Table 1 can be formulated to contain as little as 10% of the low-dose formulation or an amount greater than that up to 500% of the high dose formulation as set forth in Table 1, depending upon details known to the pharmaceutical scientist or physician.

In other embodiments, each of the components of Table 1 in compositions for parenteral administration can be formulated to contain as little as 30% of the low-dose formulation or an amount greater than that up to 300% of the high dose formulation as set forth in Table 1, depending upon details known to the pharmaceutical scientist or physician.

The skilled artisan will recognize specific medical conditions that require a deviation from these general guidelines.

According to another embodiment, the composition of the instant invention comprises ropivicaine, bupivicaine, ketorolac, dexamethasone, clonidine, ketamine, and optionally epinephrine at concentrations set forth in Table 2, or at a range from 20% of the amount in Table 2 to 500% of the amount in Table 2

TABLE 2

| Formula 003 | % wt/vol of composition |
|---|---|
| Ropivicaine | 0.18 (1.8 mg/ml) |
| Bupivicaine | 0.18 (1.8 mg/ml) |
| Ketorolac | 0.03 (300 µg/ml) |
| Dexamethasone | 0.04 (40 µg/ml) |
| Clonidine | 0.0001 (1 µg/ml) |
| Ketamine | 0.01 (100 µg/ml) |
| Epinephrine | 0.00015 (1.5 µg/ml) |

According to another embodiment, the composition of the instant invention comprises ropivicaine, bupivicaine, ketorolac, dexamethasone, clonidine, ketamine, and optionally epinephrine at concentrations set forth in Table 2, or at a range from 50% of the amount in Table 2 to 200% of the amount in Table 2

In another embodiment, a composition of the instant invention comprises at least six components as set forth in the alternative below in Table 3. The concentration of the components in Table 3 are shown in Table 1 or more narrowly, in Table 2 and Table 4.

TABLE 3

| 1 | Ropivicaine or Etidocaine |
| 2 | Bupivicaine or Levobupivicaine |
| 3 | Ketorolac or Ibuprofen |
| 4 | Dexamethasone or Methylprednisone |
| 5 | Clonidine or Dexmedetomidine |
| 6 | Ketamine or Tramdol |
| 7 | Optionally Epinephrine |

TABLE 4

| Component | % wt/vol of final composition |
|---|---|
| Etidocaine | 0.18 (1.8 mg/ml) |
| Levobupivicaine | 0.18 (1.8 mg/ml) |
| Ibuprofen | 0.20 (2 mg/ml) |
| Methylprednisone | 0.16 (160 µg/ml) |
| Dexmedetomidine | 0.00005 (0.5 µg/ml) |
| Tramdol | 0.05 (500 µg/ml) |
| Epinephrine | 0.00015 (1.5 µg/ml) |

Each of the formulations set forth in Table 5 are specifically contemplated, for example, at concentrations set forth in Table 1 (or more narrowly, in Table 2), and Table 4.

TABLE 5

| Formula # | Ropivicaine | Etidocaine | Bupivicaine | Levobupivicaine | Ketorolac | Ibuprofen | Dexamethasone | Methylprednisone | Clonidine | Dexmedetomidine | Ketamine | Tramdol |
|---|---|---|---|---|---|---|---|---|---|---|---|---|
| 004 | X | | X | | X | | X | | X | | | X |
| 005 | X | | X | | X | | X | | X | | | |
| 006 | X | | X | | X | | X | | | | X | X |
| 007 | X | | X | | X | | X | | | | | |
| 008 | X | | X | | X | X | | X | X | | X | X |
| 009 | X | | X | | X | X | | X | X | | | |
| 010 | X | | X | | X | X | X | X | | X | X | X |
| 011 | X | | X | | X | X | X | X | | X | | |
| 012 | X | | X | X | | | X | | X | | X | X |
| 013 | X | | X | X | | | X | | X | | | |
| 014 | X | | X | X | | | | | | X | X | X |
| 015 | X | | X | X | | | | | | X | | |
| 016 | X | | X | X | | | X | X | X | | X | X |
| 017 | X | | X | X | | | X | X | X | | | |
| 018 | X | | X | X | | | X | X | | X | X | X |
| 019 | X | | X | X | | | X | X | | X | | |
| 020 | X | X | | X | X | | | | X | | X | X |
| 021 | X | X | | X | X | | | | X | | | |
| 022 | X | X | | X | X | | | | | X | X | X |
| 023 | X | X | | X | X | | | | | X | | |
| 024 | X | X | X | | X | X | X | X | X | | X | X |
| 025 | X | X | X | | X | X | X | X | X | | | |
| 026 | X | X | X | | X | X | X | X | | X | X | X |
| 027 | X | X | X | | X | X | X | X | | X | | |
| 028 | X | X | X | | | | | | X | | X | X |
| 029 | X | X | X | | | | | | X | | | |
| 030 | X | X | X | | | | | | | X | X | X |
| 031 | X | X | X | | | | | | | X | | |
| 032 | X | X | X | | | | X | X | X | | X | X |
| 033 | X | X | X | | | | X | X | X | | | |
| 034 | X | X | X | | | | X | X | | X | X | X |
| 035 | X | X | X | | | | X | X | | X | | |
| 036 | | | | | X | | | | X | | X | X |
| 037 | | | | | X | | | | X | | | |
| 038 | | | | | X | | | | | X | X | X |
| 039 | | | | | X | | | | | X | | |
| 040 | | | | | X | X | X | X | X | | X | X |
| 041 | | | | | X | X | X | X | X | | | |
| 042 | | | | | X | X | X | X | | X | X | X |
| 043 | | | | | | X | X | X | | X | | |
| 044 | | | | | | X | | | X | | X | X |
| 045 | | | | | | X | | | X | | | |
| 046 | | | | | | X | | | | X | X | X |
| 047 | | | | | | | | | | X | | |
| 048 | | | | | | | X | X | X | | X | X |
| 049 | | | | | | | X | X | X | | | |
| 050 | | | | X | | | X | X | | X | X | X |
| 051 | | | | | X | | | | X | X | | |
| 052 | | | | | | | | | | | X | X |

TABLE 5-continued

| Formula # | Ropivicaine | Etidocaine | Bupivicaine | Levobupivicaine | Ketorolac | Ibuprofen | Dexamethasone | Methylprednisone | Clonidine | Dexmedetomidine | Ketamine | Tramdol |
|---|---|---|---|---|---|---|---|---|---|---|---|---|
| 053 | | X | | X | X | | X | | | | | X |
| 054 | | X | | X | X | | X | | | X | X | |
| 055 | | X | | X | X | | X | | X | X | | X |
| 056 | | X | | X | X | | | X | X | | X | |
| 057 | | X | | X | X | | | X | X | | | X |
| 058 | | X | | X | X | | | X | | X | X | |
| 059 | | X | | X | X | | | X | | X | | X |
| 060 | | X | | X | | X | X | | X | | X | |
| 061 | | X | | X | | X | X | | X | | | X |
| 062 | | X | | X | | X | X | | | X | X | |
| 063 | | X | | X | | X | X | | | X | | X |
| 064 | | X | | X | | X | | X | X | | X | |
| 065 | | X | | X | | X | | X | X | | | X |
| 066 | | X | | X | | X | | X | | X | X | |
| 067 | | X | | X | | X | | X | | X | | X |

"X" indicates the presence of the component in the formula (i.e. composition)

Therapeutic Compositions and Administration of Instant Compositions

Administration Routes

The instant invention provides compositions in a pharmaceutically acceptable dosage and dose form.

Administration of the present compositions to achieve therapeutic effect may be any parenteral route, e.g. periarticular, intra-articular, intrabursal, interscalene, intradiscal, transdermal, intradermal, transmucosal, subcutaneous, intrathecal, epidural, caudal, periodontal, or intramuscular administration. Certain clinical situations may require administration of the present compositions as a single effective dose, or may be administered as multiple doses or multiple locations.

Dosage Forms

Instant compositions are pharmaceutically acceptable, moreover, some embodiments are acceptable for parenteral administration, others for intravenous administration, and others for topical administration. The skilled pharmaceutical scientist readily knows how to add excipients, etc., to make the composition administratable by the intended route. Optionally instant compositions are administered to patients in a pharmaceutically acceptable form containing physiologically acceptable carriers, excipients or diluents. Such diluents and excipients may be comprised of buffers, salts, antioxidants (for example ascorbic acid), low molecular weight polypeptides (for example polypeptides ≤10 amino acids) amino acids, carbohydrates (for example, glucose, dextrose, sucrose, or dextrans), chelating agents such as EDTA, stabilizers (such as glutathione). Additionally, co-substrates for the Instant Compositions, for example, calcium ($Ca^{2+}$) may be administered at time of dosage for maximal activity of the enzyme. Such carriers and diluents are nontoxic to the patient at recommended dosages and concentrations.

Optionally, instant compositions are administered to patients in a dermatologically acceptable topical form.

Kits

The technology provided herein also includes kits for use in the present methods.

In one embodiment, the kit comprises a sterile multi-draw container containing a 30 to 100 ml aliquot of an instant composition that has been lyophilized, a sterile multi-draw container containing a 30 to 100 ml of sterile water, a 30 to 100 ml sterile syringe with a 18 to 24 gauge needle, one or more 3 to 100 ml sterile syringes, and instruction to reconstitute the instant compositions with the sterile water.

In another embodiment, the kit contains a vial labeled "A", a vial labeled "B" and a 30 to 100 ml sterile syringe with a 18 to 24 gauge needle as well as instructions for mixing according to Example 3.

Dosing Frequency

In some embodiments, a single dose of a composition according to the technology is administered to a subject. In other embodiments, one or more doses are administered at multiple sites, e.g. 2 to 10, or 3 to 10, or 4 or more, or 5 or more. In some embodiments, one or more doses are administered over two or more time points, separated by minutes, hours, days, weeks, or more.

Dosing

Dosage requirements of the present compositions may vary significantly depending on administration site, nature of pain, age, race, weight, height, gender, duration of treatment, methods of administration, biological activity of the compositions, and severity of condition or other clinical variables. Effective dosages may be determined by a skilled physician or other skilled medical personnel.

By way of example, for intraarticular injection, volumes may range from 1 ml to 83.3 ml at each site.

By way of example, for nerve block, volumes may range from 5 ml to 30 ml.

Uses of the Instant Compositions

In one embodiment, instant compositions are useful for infiltration anesthesia, field block anesthesia, regional anesthesia, peripheral nerve block, plexus anesthesia (plexus block), epidural (extradural) anesthesia, spinal anesthesia (e.g. subarachnoid block), local anesthesia, and transincision catheter anesthesia.

In one embodiment, instant compositions are useful for nerve blocks, for example, peripheral nerve blocks, extradural nerve blocks, neuraxial nerve block, retrobulbar nerve block, and transversus abdominis plane (TAP) block.

In one embodiment, instant compositions are useful for joint arthroscopy and arthroplasty (e.g., hip, knee, shoulder, and ankle).

In another embodiment, instant compositions are used for infiltration anesthesia for achilles tendon repair.

In one embodiment, instant compositions are useful for surgical treatment of surgical repair of bone, osteomoty, bone osteochondroma malformation, orofacial surgery, tooth extraction and prosthetic implantation, anterior cruciate ligament harvest, allografts, and/or bone tendon bone grafts.

In one embodiment, instant compositions are useful adjunct to repair of incisional hernias, as adjunct to anterior cruciate ligament reconstruction, for bursectomy excision, and/or hip arthroscopy.

Instant compositions are usefully administered by infiltration throughout a wound at the time of surgery.

In another embodiment, analgesic effect duration is prolonged by the placement of a catheter to the surgical site for postoperative administration of present compositions.

Unexpected Findings

Without be bound by theory, the inventor believes that the superior action of the instant compositions are the result of a complex interaction of components and an interaction between metabolic pathways leading to quick onset of total pain control, long duration, and minimal toxicity or side effects. The specific combinations taught here are the result of inventor insight and empirical observations.

Long acting aminoamide local anesthetics of the instant compositions bind to and block voltage gated Na+ channels in sensory nerves. Moreover, they reduce the transmission of the advancing wave of depolarization down the length of the nerve. In part, the duration of action of instant aminoamide local anesthetics is due to their high lipid solubility, which allows them to remain in lipid bilayers at target sites—rather than being removed by the microvasculature. However, greater hydrophobicity also results in greater toxicity. Through insight of the inventor and empirical observations, certain preferred combinations of the at least two long acting aminoamide local anesthetics are taught here.

In the instant compositions, the efficacy and duration of the long acting aminoamide local anesthetics is further increased by the vasoconstrictive action of a corticoid steroid, an NSAID, and optionally epinephrine. Each of these components is vasoconstrictive through a different mechanism. For example, the NSAID(s) of the instant composition blocks prostaglandin synthesis by blocking cyclooxygenase-2. PGE2 is one of such prostaglandins and is a potent vasodilator. Corticosteroids enhance the vasoconstrictor actions of endogenous or pharmaceutical norepinephrine and angiotensin II. The optional epinephrine of the instant compositions, causes vasoconstriction through the α1 adrenergic receptor-dependant pathway. The interaction of between these multiple pathways results in an especially effective vasoconstriction and efficacy of the analgesic components.

Tissue damage, resulting from surgery, causes an activation of prostaglandins which, as discussed above, causes vasodilatation. It should also be noted that prostaglandins also have an effect on pain. At higher concentrations, prostaglandins cause pain by direct action on the nerve endings; at lower concentrations, they reducer the pain threshold. Accordingly, the NSAID(s) of the instant compositions and corticosteroids of the instant compositions, by blocking prostaglandin synthesis, function to block pain and raise the pain threshold.

The inventor believes that at sufficient concentrations, adrenergic receptor agonists as taught here, can partially inhibit voltage-gated Na+ and K currents and shift the steady-state inactivation curve to more negative potentials. In concert with the action of the two (or more) long acting aminoamide local anesthetics, voltage-gated channels are inhibited to a surprising level.

The inventor believes that at sufficient concentrations, the N-methyl-D aspartate receptor antagonist of the instant compositions antagonize neurotransmitters glutamate and glycine and prevent hyperpolarization and drive the membrane potential away from the threshold for firing an action potential. Without being bound by theory, the inventor believes that there is a potentiation of duration and efficacy of amide local anesthetics when combined as taught here.

The addition of the instant alpha 2 adrenergic receptor agonist has a surprisingly impact on the total anti-nociceptive effects (efficacy and duration) of the composition, presumably involving other central pathways (i.e. an enkephalin mediated pathway).

The superior properties, as believed through insight of the inventor, can only be understood in part by the above description of the metabolic pathways.

The superior properties of instant compositions include superior analgesia, duration of analgesia (long acting), safety, narcotic sparing, and motor sparing properties.

Through insight of the inventor, the instant compositions are also superior in one or more of the following benefits: reduction in anesthetic requirements, reduction or elimination of need for parenteral narcotics, reduction in post operative nausea and vomiting, more rapid recovery from anesthesia, decrease in motor weakness, increased mobility, reduction of venus thromboembolism, and increased patient overall satisfaction.

EXAMPLES

Example 1. Formulating Present Compositions by Admixing

The following procedure is performed in a sterile manner using methods well-known to the pharmaceutical scientist or appropriate medical professionals. The individual components of the formulation are obtained as commercially available pharmaceutical products and the amounts of each component are delivered in a sterile manner (e.g. by sterile syringe) according to Table 6 and delivered into a sterile multi-draw stoppered vial. The components of the vial are mixed by swirling. At time of administration, sterile aliquots are loaded into an appropriately-sized syringe. This is a representative formulation method and produces Formula 003.

TABLE 6

| Component | Volume and weight of component | Dose per ml of final composition | % wt/vol composition |
|---|---|---|---|
| Bupivicaine w/ epi 1:200 | 150 mg in 30 ml | 1.8 mg | 0.18 |
| Ropivicaine | 150 mg in 30 ml | 1.8 mg | 0.18 |
| Ketorolac | 30 mg in 1 ml | 0.36 mg | 0.036 |
| Clonidine | 100 mcg in 1 ml | 1.2 mcg | 0.00012 |
| Dexamethasone | 4 mg in 1 ml | .05 mg | 0.005 |
| Ketamine | 10 mg in 0.2 ml. | 12 mg | 0.012 |
| Epinephrine (from commercial bupivicaine preparation) | 150 mcg | 1.8 mcg | 0.018 |
| Saline | Q.S. to 83.2 ml | | |

Example 2. Formulating Present Compositions by Lyophilization

The following procedure is performed in a sterile manner using methods well-known to the pharmaceutical scientist or appropriate medical professionals. The components of the formulation are obtained as commercially available pharmaceutical products and the amounts of each component are delivered in a sterile manner (e.g. by sterile syringe) into a sterile lyophilization tube in amounts set forth in Table 6. The composition is frozen to $-70^C$ and are subjected to vacuum (in a typical commercial lyophilizer) for sufficient time for sublimation of all the liquid. Next, the lyophilized material is transferred to a sterile, multidraw stoppered vial and stored at −70 C until needed. The vial is placed in a box with instructions to reconstitute by addition of 30 ml of distilled, sterile water. This is a representative formulation method and produces Formula 003.

Example 3. Formulating Present Compositions by the Two Vial Method

"Vials A and B" are filled according to Table 7. Buffer A is a sterile, pharmaceutically acceptable buffer useful at acidic pH (e.g. the pH of 5.0); Buffer B is useful at somewhat alkaline pH (e.g. ph of 7.5). Buffer A and Buffer B are compatible when combined and result in an appropriate final pH. Useful mixed buffer systems are well known in the art.

The vials are stored at 4° C. until use.

At the time of surgery, the contents of Vial A is removed by sterile syringe and added to Vial B and the solutions (in Vial B) are mixed. The formulation method results in remarkable stability. This is a representative formulation method and produces Formula 003

TABLE 7

| Ingredient | ml | mg of component | Dose per ml of final composition (vial A + B) | % wt/vol final composition |
|---|---|---|---|---|
| Vial A | | | | |
| Bupivicaine w/ epi 1:200 | 30 | 150 mg | 1.8 mg | 0.18 |
| Ropivicaine | 30 | 150 mg | 1.8 mg | 0.18 |
| Clonidine | 1 | 100 μg | 1.2 mcg | 0.00012 |
| Ketamine | 0.2 | 10 μg | 12 mg | 0.012 |
| Epinephrine | | 150 μg w/ Bupivicaine | 1.8 mcg | 0.018 |
| Buffer A (Q.S. to 70) | | | | |

TABLE 7-continued

| Ingredient | ml | mg of component | Dose per ml of final composition (vial A + B) | % wt/vol final composition |
|---|---|---|---|---|
| Vial B | | | | |
| Ketorolac | 1 ml | 30 mg | 0.36 mg | 0.036 |
| Dexamethasone | 1 ml | 4 mg | .05 mg | 0.005 |
| Buffer B (Q.S. to 13.2) | | | | |

Example 4. Administration in Conjunction with Total Knee Replacement

The following procedure is useful for pain management by administration of instant compositions for total knee replacement. All patients are given spinal anesthesia.

The instant composition of Example 1 is prepared as set forth above. The first injection is performed at once after femoral and tibial cuts are made. Three to five small subsequent injections are made, using approximately 15 ml total of an instant composition in the popliteal fossa, aspirating as necessary at this injection site to avoid intra-vascular injection. After the prosthetic implants are set, the next injections are administered to the medial and lateral periosteum of both the femur and the tibia, using approximately 20 ml of an instant composition.

Subsequently, the medial and lateral gutters are injected with 10 ml of an instant composition on each side after patella preparation. Next, the peripatellar area and the skin are injected prior to closing the incision, using approximately 10 ml of an instant composition. The remaining amount of an instant composition is administered to the skin incision covering the superior aspect of the incision at the subcutaneous level.

Results.

During the study period, narcotic pain requirements, manipulation rates, and the need for prolonged physical therapy were significantly reduced as compared to historical controls. Recovery of functional milestones and ROM was achieved at an earlier period in 90% of patients. Overall patient satisfaction was greatly improved.

By controlling acute pain in the critical early postoperative period (three days) following total knee replacement, the pain management protocol allowed for improved recovery of functional milestones and improved patient satisfaction. It appears that pain control plays a much larger role in functional recovery than incision length.

Example 5. Experimental Clinical Study of Use for Arthroplasty

Over the period of about one year, 45 total hip replacements and 85 total knee replacements were performed with a periarticular injection of Formula 003 prepared as set forth in Example 1. All patients were given spinal anesthesia and total knee arthroplasty (i.e. a surgical procedure in which parts of the knee joint are replaced with artificial parts; "TKA") patients received an adductor canal block. Multimodal oral and intravenous medications were administered and parenteral narcotics were not used during the preoperative course.

Procedure

Intraoperatively, surgical procedures were performed in line with traditional surgical approaches and techniques. The total knee replacements were generally performed according to Example 4. Prior to closure, Formula 003 was injected into the surgical field.

Patients were followed with postoperative pain scales and monitored for narcotic requirements and complications. Additionally, patient assessment was performed by skilled nursing and physical therapy in home to document recovery of functional status, such as unassisted walking, stair-climbing, range-of-motion (ROM), and overall satisfaction.

Results

During the study period, narcotic pain requirements, manipulation rates, and the need for prolonged physical therapy were significantly reduced. Skilled Nursing visits were on average 3 and PT visits appear to being able to be reduced to 7 or less home visits.

Recovery of functional milestones and range of motion was achieved at an earlier period in most of patients. Pain scores were on average 1.07 upon discharge from the facility using a 0-10 Visual Analog Scale. Pain from postoperative day ("POD") 0 scores were 3.3. POD 1 pain scores were 3.6. POD 2 pain scores were 3.8 on average. Multimodal protocols including the use of Oxycontin 10 mg every 12 hours were administered as part of the protocol. Average length of stay was 338 min from admission to discharge from facility to home. Patients ambulated prior to discharge in the surgery center and were not braced due to adequate motor function. Infection rates were reported at less than 1%. Estimated blood loss was <100 ml in all cases but 1, in which the estimated blood loss was 200 ml. There were no hospital transfers during the study and none yet to date in the program. There have been no blood transfusions to date. Overall patient satisfaction was positive.

Each of these results set forth above were remarkable compared to previously published studies and based upon the experience and judgment of surgeons participating in this study when compared to analgesia of different forms and different formulations representing the current standard of care. The economic impact was also believed to be remarkable.

Utilizing an instant composition to control acute pain in the critical early postoperative period (48-72 hours) following total hip and total knee replacement, has allowed for improved recovery of functional milestones and improved patient satisfaction. It appears that instant compositions play a large role in the recovery of the total joint patient in the ambulatory setting. Instant composition's early and rapid onset yet apparent 48-72 duration appears to be the most important component allowing for early and rapid discharge after total joint replacement.

Example 6. Post Operative Assessments

Post operative assessments that are useful for demonstrating the superiority of instant compositions and set forth in Table 8. Through insight of the inventor, each of these assessment parameters can be used to demonstrate the unexpected superiority of the instant compositions over standard (state of the medical arts) analgesia compositions.

TABLE 8

|  | Day 1 | Day 2 | Day goal achieved |
|---|---|---|---|
| Range of motion | record | record | record |
| Walk on flat surface | In meters | In meters | 100 meters |

TABLE 8-continued

| | Day 1 | Day 2 | Day goal achieved |
|---|---|---|---|
| Western Ontario and MacMaster Universities Osteoarthitis Index (WOMAC Pain Score) | record | record | record |
| blood loss | record | record | |
| Pain meds | record | record | record |
| Nausea/vomiting | record | record | record |
| itching | record | record | record |
| drowsiness | record | record | record |
| urinary retention. | record | record | record |
| ileus | record | record | record |
| Days until prosthesus failure | | | record |
| Hospital for Special Surgery Knee Score (HSS) | record | record | record |
| Knee Society's Clinical and Functional Scoring System (KSS) | record | record | record |
| Harris Hip Score (HHS) | record | record | record |
| time for rescue analgesia | | | record |

All publications and patents referenced in this specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the technology as claimed should not be unduly limited to such specific embodiments. Indeed, various modifications of the described modes for carrying out the technology that are obvious to those skilled in pharmacology, biochemistry, medical science, or related fields are intended to be within the scope of the following claims.

What is claimed is:

1. A pharmaceutically acceptable medicament comprising ropivicaine, bupivicaine, ketorolac, dexamethasone, clonidine, and ketamine.

2. The medicament of claim 1, further comprising epinephrine.

3. The medicament of claim 1 wherein the concentration of ropivicaine is 1.125 mg/ml to 2.5 mg/ml; the concentration of bupivicaine is 1.125 mg/ml to 2.5 mg/ml, the concentration of ketorolac is 100 µg/ml to 400 µg/ml, the concentration of dexamethasone is 20 µg/ml to 100 µg/ml; the concentration of clonidine is 0.5 µg/ml to 2 µg/ml, the concentration of ketamine is 50 µg/ml to 500 µg/ml; and optionally the medicament further comprises epinephrine at a concentration of 1 µg/ml to 3 µg/ml.

4. The medicament of claim 1 wherein the concentration of ropivicaine is 80% to 120% of 1.8 mg/ml; the concentration of bupivicaine 80% to 120% of 1.8 mg/ml; the concentration of ketorolac is 80% to 120% of 300 µg/ml; the concentration of dexamethasone is 80% to 120% of 40 µg/ml, the concentration of clonidine is 80% to 120% of 1 µg/ml; the concentration of ketamine is 80% to 120% of 100 µg/ml; and optionally the medicament further comprises epinephrine at a concentration of 80% to 120% of 1.5 µg/ml.

5. The medicament of claim 1 wherein: the concentration of ropivicaine is 0.1125 mg/ml to 12.5 mg/ml; the concentration of bupivicaine is 0.1125 mg/ml to 12.5 mg/ml, the concentration of ketorolac is 10 µg/ml to 2,000 µg/ml; the concentration of dexamethasone is 2 µg/ml to 500 µg/ml, the concentration of clonidine is 0.05 µg/ml to 10 µg/ml; the concentration of ketamine is 5 µg/ml to 2,500 µg/ml, and optionally the medicament further comprises epinephrine at a concentration of 0.1 µg/ml to 15 µg/ml.

6. A method of treatment or management of pain comprising the step of administering a medicament of claim 1 to a subject in need thereof wherein the medicament optionally further comprises epinephrine.

7. The method of claim 6 wherein the administering step comprises an injection into one or more sites in a region where trauma has been created by a surgery.

8. The method of claim 7 wherein the method reduces pain.

9. The method of claim 8 wherein the pain is postoperative pain.

10. The method of claim 6 wherein the administering step is performed in a nerve block procedure.

11. The method of claim 10 wherein the nerve block procedure comprises one or more members of the group consisting of a peripheral nerve block, an extradural nerve block, a neuraxial nerve block, a retrobulbar nerve block, and a transversus abdominis plane block.

12. The method of claim 6 where the administering step is performed in an anesthesia procedure.

13. The method of claim 12 wherein the anesthesia procedure comprises one or more members of the group consisting of field block anesthesia, regional anesthesia, peripheral nerve block, plexus anesthesia, epidural anesthesia, extradural anesthesia, spinal anesthesia, local anesthesia, or transincision catheter anesthesia.

14. The method of claim 6 wherein the administering step is performed in a joint selected from the group consisting of hip, knee, shoulder, and ankle.

15. The method of claim 6 wherein the step of administering the medicament comprises an infiltration step for a joint arthroscopy or an arthroplasty or both.

16. A kit comprising a first vial and a second vial, wherein the first vial contains bupivicaine, ropivicaine, clonidine, ketamine, a suitable pharmaceutically acceptable buffer and optionally epinephrine and the second vial contains ketorolac, dexamethasone, and a suitable pharmaceutically acceptable buffer, and wherein the kit further comprises written instructions for how to combine the contents of the first vial and the contents of the second vial and optionally one or more sterile syringes.

17. The method of claim 6 wherein the administering step comprises an injection via a parenteral route.

18. The method of claim 17 wherein the parenteral route is selected from the group of routes consisting of periarticular, intra-articular, intrabursal, interscalene, intradiscal, transdermal, intradermal, transmucosal, subcutaneous, intrathecal, epidural, caudal, periodontal, and intramuscular.

19. The method of claim 10 wherein the nerve block procedure is selected from the group consisting of extradural nerve block, neuraxial nerve block, retrobulbar nerve block, and transversus abdominis plane block.

* * * * *